(12) United States Patent
Ajayaghosh et al.

(10) Patent No.: US 8,344,150 B2
(45) Date of Patent: Jan. 1, 2013

(54) PYRROLE END-CAPPED BIPYRIDINE ASSAY POWDER FOR SELECTIVE DETECTION OF ZINC IONS AND A PROCESS FOR THE PREPARATION THEREOF

(75) Inventors: Ayyappanpillai Ajayaghosh, Kerala (IN); Sivaramapanicker Sreejith, Kerala (IN)

(73) Assignee: Council of Scientific & Industrial Research, New Delhi (IN)

( * ) Notice: Subject to any disclaimer, the term of this patent is extended or adjusted under 35 U.S.C. 154(b) by 58 days.

(21) Appl. No.: 12/811,008

(22) PCT Filed: Jun. 13, 2008

(86) PCT No.: PCT/IN2008/000374
§ 371 (c)(1),
(2), (4) Date: Jun. 28, 2010

(87) PCT Pub. No.: WO2009/084007
PCT Pub. Date: Jul. 9, 2009

(65) Prior Publication Data
US 2010/0284858 A1   Nov. 11, 2010

(30) Foreign Application Priority Data
Dec. 28, 2007   (IN) .......................... 2748/DEL/2007

(51) Int. Cl.
*C07D 401/00* (2006.01)
(52) U.S. Cl. .................................................. 546/276.1
(58) Field of Classification Search .................. None
See application file for complete search history.

(56) References Cited

U.S. PATENT DOCUMENTS
6,406,862 B1   6/2002   Krakauer

OTHER PUBLICATIONS

Ajayaghosh, A. et al J. Amer. Chem. Soc. 2005 vol. 127, pp. 14962-14963 and supporting material pp. S1-S812520237.*
CASREACT Accession No. 148:495745 2007.*
Jiang, et al., "Fluorescent Detection of Zinc in Biological Systems: Recent Development on the Design of Chemosensors and Biosensors," Coordination Chemistry Reviews, 2004, pp. 205-229, vol. 248.
Lim, et al., "Illuminating Zinc in Biological Systems," Chemistry—A European Journal, 2005, pp. 38-49, vol. 11.
Berg, et al., "The Galvanization of Biology: A Growing Appreciation for the Roles of Zinc," Science, 1996, pp. 1081-1085, vol. 271.
Cuajungco, et al., "Zinc Metabolism in the Brain: Relevance to Human Neurodegenerative Disorders," Neurobiology of Disease, 1997, pp. 137-169, vol. 4.
Mattson, "Pathways Towards and Away from Alzheimer's Disease," Nature, 2004, pp. 631-639, vol. 430.
Citron, "Strategies for Disease Modification in Alzheimer's Disease," Nature Reviews—Neuroscience, 2004, pp. 677-685, vol. 5.
De Onis, et al., "Is Malnutrition Declining? An Analysis of Changes in Levels of Child Malnutrition Since 1980," Bulletin of the World Health Organization, 2000, pp. 1222-1233, vol. 78.
Carol, et al., "Ratiometric and Near-Infrared Molecular Probes for the Detection and Imaging of Zinc Ions," Chemistry—An Asian Journal, 2007, pp. 338-348, vol. 2.
Takahashi, et al., "Test Strips for Heavy-Metal Ions Fabricated from Nanosized Dye Compounds," Angewandte Chemie International Edition, 2006, pp. 913-916, vol. 45.
Sreejith, et al., "Detection of Zinc Ions Under Aqueous Conditions Using Chirality Assisted Solid-State Fluorescence of a Bipyridyl Based Fluorophore," Chemical Communications, 2008, pp. 2903-2905.

* cited by examiner

*Primary Examiner* — Janet L. Andres
*Assistant Examiner* — Heidi Reese
(74) *Attorney, Agent, or Firm* — Blank Rome LLP

(57) ABSTRACT

The present invention provides pyrrole end-capped bipyridine derivative having a general formula (1) useful for the detection of zinc ions in solution. The present invention also provides a process for the preparation of pyrrole end-capped bipyridine derivative having a general formula (1). The present invention further provides a dipstick device by coating the assay powder of formula (1) in alumina over a thermoplastic or a glass solid support. The detection event can be monitored by noting the color change and the intense fluorescence change on the surface of the dipstick. For zinc ions, in addition to the color change an intense fluorescence change from greenish-yellow to red is observed. Detection event by means of fluorescence change is selective for $Zn^{2+}$ ions when compared with all other biologically important metal ions like $Na^+$, $K^+$, $Ca^{2+}$; $Mg^{2+}$, $Cu^{2+}$. The present dipstick is reusable, and can conduct the analysis of different samples using same stick.

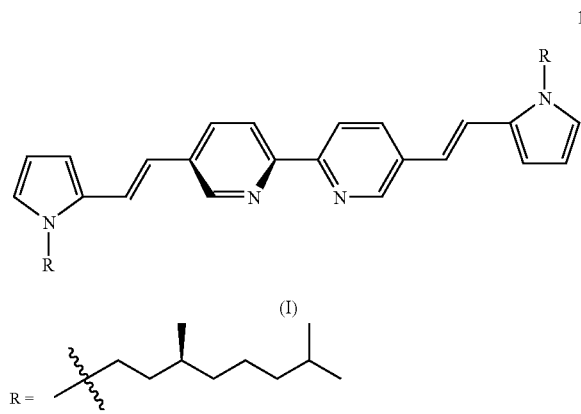

15 Claims, 8 Drawing Sheets

Figure 1:
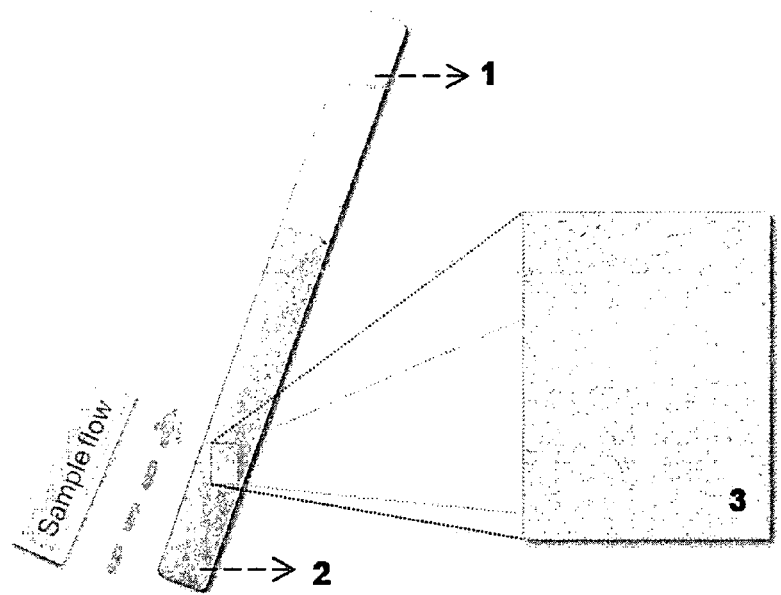

Figure 3
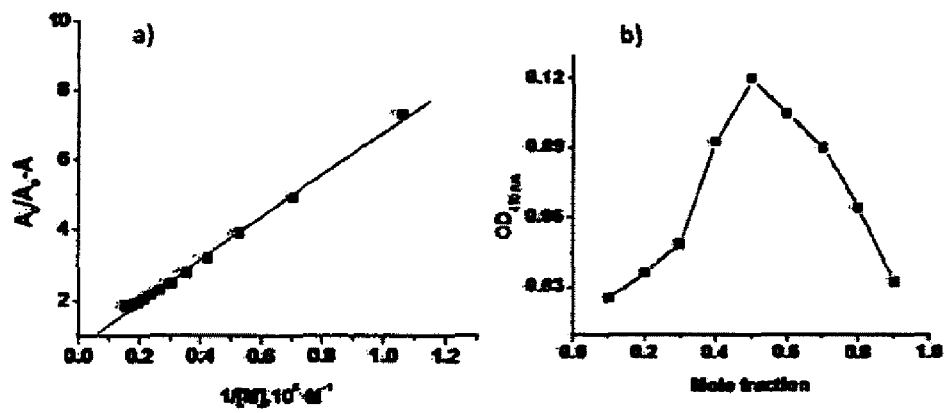
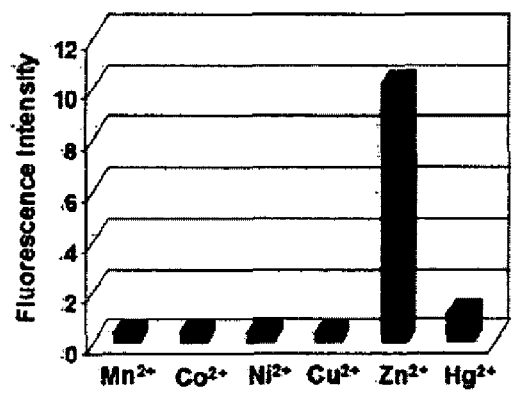
Figure 4

PYRROLE END-CAPPED BIPYRIDINE ASSAY POWDER FOR SELECTIVE DETECTION OF ZINC IONS AND A PROCESS FOR THE PREPARATION THEREOF

FIELD OF THE INVENTION

The present invention relates to pyrrole end-capped bipyridine assay powder of formula 1 useful for the selective detection of zinc ions.

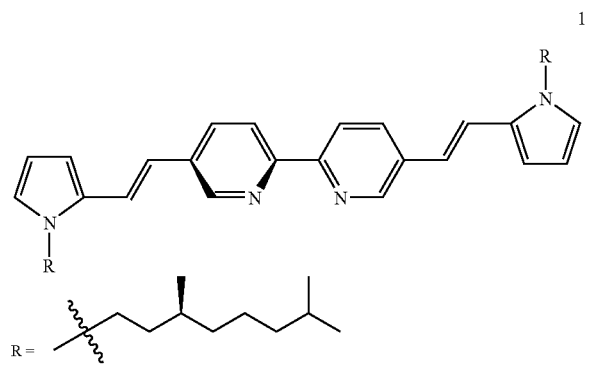

The present invention also provides a process for the preparation of pyrrole end-capped bipyridine assay powder of formula 1 useful for the selective detection of zinc ions. This assay powder can be used as a coating over a plastic/glass/paper back support for the fabrication of dipstick devices. Thereby prepared device in particular can be used for selective detection of zinc ions ($Zn^{2+}$) from samples containing different metal ions.

BACKGROUND OF THE INVENTION

Zinc is the second most abundant transition metal ion in the human body, where it has multiple roles in both intra and extra cellular functions. A large number of proteins and enzymes were identified to contain $Zn^{2+}$. Zinc is reported to be responsible for neurological disorders such as Alzheimer's disease (AD), amyotropic lateral sclerosis (ALS), Parkinson's disease and Epilepsy. Alzheimer's disease is a neurodegenerative disease associated with aggregation of β-amyloid peptides (Aβ) in the brain. $Aβ_{1-42}$ has a high affinity to metal ions and forms insoluble aggregates particularly in the presence of metal ions like $Zn^{2+}$, $Cu^{2+}$ and $Fe^{2+}$. In addition, zinc plays crucial role in insulin secretion and apoptosis. The World Health Organization estimates that more than 40% of the children in Africa and Asia have stunned growth associated with limited dietary zinc. The extent to which zinc deficiency conditions persist today is difficult to estimate because of the lack of suitable biochemical markers for zinc.

Besides growth, numerous body functions are affected by zinc ions, including immune, endocrine and gastro-enterological systems. The huge scope for the exploration of the diverse physiological roles of biological zinc demands sensitive and non-invasive technique for the real time detection and imaging. The relative concentration of free $Zn^{2+}$ within biological cells varies from 1 nM in the cytoplasm of many cells to 1 mM in the vesicles of presynaptic neurons in human brain. Although the total concentration of the zinc in a cell is relatively high, the concentration of the free zinc, which is not strongly bound to proteins, is extremely low. The estimation of the free zinc has been proved to be difficult using classical methods. These concerns have been on the top priority of chemists to develop selective and efficient probes or the so called chemosensors for zinc ions.

Since $Zn^{2+}$ is silent to most of the analytical techniques, fluorescent techniques stand out as a method of choice. This method utilizes a probe molecule that recognizes $Zn^{2+}$ and emits specific wavelength upon binding, which in turn allows tracking of zinc ions in live cells using fluorescence microscopy. A fluorescent molecular probe consists of a fluorophore attached to a chelating agent or an ionophore with or without a spacer group. A change in the fluorescence intensity or wavelength occurs as a result of an analyte binding which results in a signal output and can be studied spectroscopically. An effective chemosensor must convert the event of cation recognition by the ionophore into an easily monitored and highly sensitive light signal from the fluorophore. References may be made to: a) P. Jiang, Z. Guo, Coord. Chem. Rev. 2004, 248, 205-229; b) N. C. Lim, H. C. Freake, C. Brückner, Chem.-Eur. J. 2005, 11, 38-49; c) J. M. Berg, Y. Shi, Science 1996, 271, 1081-1085; d) M. P. Cuajungco, G. J. Lees, Neurobiol. Dis. 1997, 4, 137-169; e) M. Mattson, Nature, 2004, 430, 631; f) M. Citron, Nat. Rev. Neurosci, 2004, 5, 677; g) M. de Onis, E. A. Frongillo, M. Blössner, Bull. World Health Organ. 2000, 78, 1222-1233; h) P. Carol, S. Sreejith, A. Ajayaghosh, Chem. Asian J., 2007, 2, 338-348.

Reference may be made to Ajayaghosh, P. Carol, S. Sreejith, J. Am. Chem. Soc., 2005, 127, 14962-14963 wherein the fluorophores 2a-c (formula 2) showed strong emission around 537 nm in acetonitrile with a quantum yield of 0.4. In buffered (HEPES, pH=7.2) acetonitrile-water mixture (9:1 v/v), titration of transition metal salts to 2c showed strong quenching of the emission at 547 nm except in the case of $Zn^{2+}$ which resulted in a red-shifted emission at 637 nm. Alkali and alkaline earth metal salts could not induce any considerable changes to the emission behavior of 2a-c. The binding of $Zn^{2+}$ was highly selective in the presence of a variety of other metal ions. Though $Cu^{2+}$ quenches the emission of 2c, in the presence of $Zn^{2+}$ a red emission prevails indicating the preference of 2c towards $Zn^{2+}$. The selective visual sensing of $Zn^{2+}$ with a red emission is ideally suited for the imaging of biological specimens.

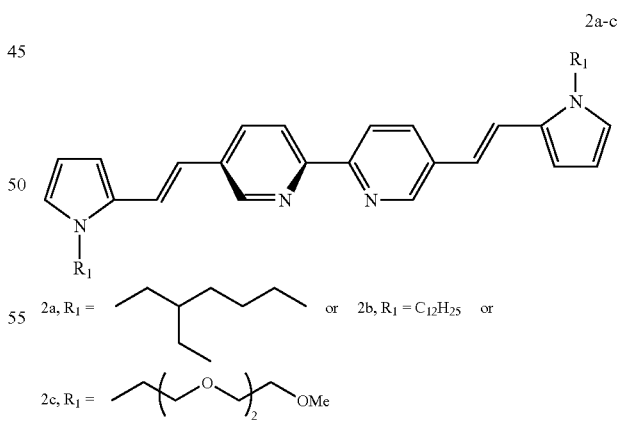

However, the other derivatives of formula 2a-c, act as ratiometric sensors for $Zn^{2+}$ ions only in organic/aqueous solvents and not in the solid state and this prevented the practical use of these derivatives.

The main disadvantages which have prevented the practical application of molecular probes for the detection of metals ions in aqueous media at normal conditions are;

1) The first disadvantage is that the detection still requires professional laboratory type operations, such as precise transfer of solutions, usage of sophisticated instrumental techniques etc., making it less useful to people who do not have any scientific background.

2) Second is the low sensitivity and selectivity Of the probes towards metal ions for an instrument free observation of binding events. For example, distinguishing analyte binding event by color change or fluorescence change with naked eye.

3) Third one is related to the property of the fluorophore. The selected fluorophore must be water insoluble and at the same time it should interact with metal ions in the solution. An ideal fluorophore must have comparatively good quantum yield in solid state and 4) The fourth and significant one is the difficulty in reprocessing and thereby multiple use of the probe.

OBJECTIVES OF THE INVENTION

The main object of the present invention is to provide pyrrole end-capped bipyridine assay powder of formula 1 useful for the selective detection of zinc ions in solutions.

Another object of the present invention is to provide a process for the preparation of pyrrole end-capped bipyridine assay powder of formula 1 useful for the selective detection of zinc ions in solutions.

Yet another object of the present invention is to provide a virtually flawless technique for detecting metal ions using a relatively simple and convenient technique, specifically required for the practical application of molecular probes as sensors for metal ions such as $Zn^{2+}$.

Yet another, object of the present invention is to provide a simple dipstick device for the selective detection of zinc ions using a pyrrole end-capped bipyridine assay (formula 1).

Yet another object of the present invention is to provide an accurate, fast, real time method for assaying $Zn^{2+}$ ions in aqueous samples.

SUMMARY OF THE INVENTION

Accordingly the present invention provides Pyrrole end capped bipyridine assay powder of Formula 1 useful for the selective detection of $Zn^{2+}$ ions in solution.

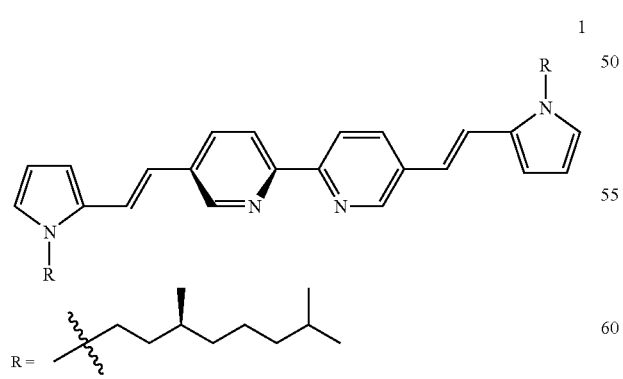

In an embodiment of the present invention the Pyrrole end capped bipyridine assay powder of formula 1 is useful for the selective detection of $Zn^{2+}$ ions in aqueous or organic solution.

The present invention further provides a process for the preparation of Pyrrole end capped bipyridine assay powder of formula 1

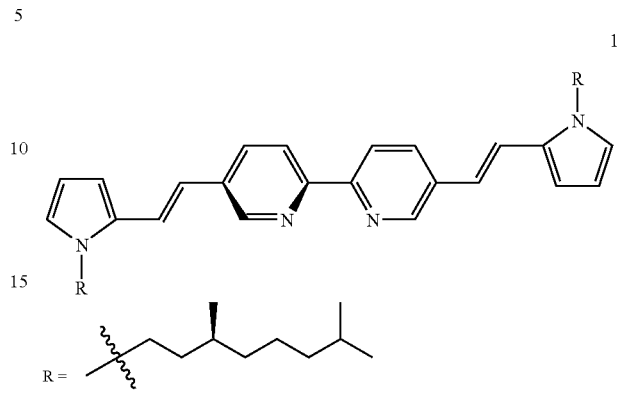

and said process comprising the steps of:
a) preparing 5,5'-bis(bromomethyl)-2,2'-bipyridine by reacting 5,5'-dimethyl-2,2'-bipyridine in dry carbon tetrachloride in the presence of N-bromosuccinimide by known method,
b) preparing 5,5'-Bis-(diethyl phosphonomethyl)-2,2'-bipyridine by reacting 5,5'-bis(bromomethyl)-2,2'-bipyridine obtained in step (a) with triethyl phosphite by known method,
c) reacting 5,5'-Bis-(diethyl-phosphonomethyl)-2,2'-bipyridine obtained obtained in step (b) with N-alkylpyrrole-2-carboxaaldehyde of formula 1'

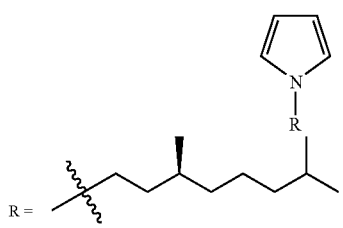

in a molar ratio of 1:2 to 1:3, in the presence of sodium hydride in dry tetrahydrofuran (THF), under reflux, for a period of 10 to 20 hours, cooling the above said reaction mixture to a temperature of 25° C. to 35° C. and removing the THF solvent under reduced pressure to obtained a pasty residue, suspending the above said resultant residue in water and extracting it with dichloromethyl, followed by washing the organic layer with brine, drying and concentrating it to obtain the crude product, followed by purification by known method to obtain the desired product.

In an embodiment of the present invention the molar ratio of bisphosphonate to N-alkylpyrrole-2-carboxaaldehyde used in step (c) is preferably 1:2.

In yet another embodiment the reaction time period used in step (c) is preferably in the range of 12 to 14 hours.

In yet another embodiment the yield of the pyrrole end capped bipyridine assay powder of Formula 1 obtained is in the range of 40% to 45%.

In yet another embodiment the pyrrole end capped bipyridine assay powder of Formula 1 exhibit a highly greenish yellow solid state illumination.

In yet another embodiment the pyrrole end capped bipyridine assay powder of Formula 1 exhibits strong emission in acetonitrile at about 537 nm at a quantum yield of 0.4.

In yet another embodiment the pyrrole end capped bipyridine assay powder of Formula 1 is useful for the detection of $Zn^{2+}$ ions in solution form.

The present invention further provides a dipstick device useful for the selective detection of $Zn^{2+}$ ions in solution comprising i) pyrrole end capped bipyridine assay powder of Formula 1 adsorbed over the ceramic powder preferably alumina;

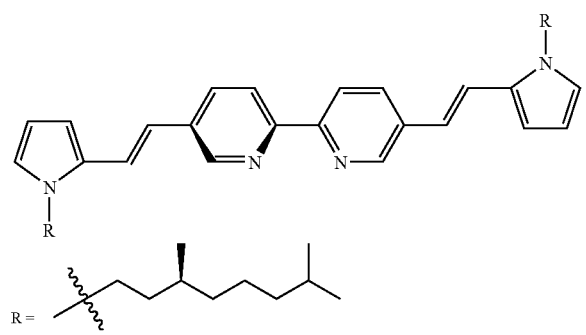

1 ii) the said material of step (i) being deposited or fixed over the surface of a strip support.

In an embodiment of the present invention the strip support used is made of plastic, glass or paper backing.

In yet another embodiment the dipstick device is useful for the detection of $Zn^{2+}$ ions in solution.

In still another embodiment the dipstick device is useful for the analytical sample containing lowest metal ions concentration of $5 \times 10^{-4}$ M.

The dipstick has particular application to metal ion containing aqueous samples and the detection event can be conducted at the location where the sample is found and this does not require any sophisticated technical support. The solution containing $Zn^{2+}$ ions will result in the color change of the solid support where the presence of intense color will indicate high levels of $Zn^{2+}$ in the sample and a faint color indicate low levels of $Zn^{2+}$ in the sample. The stick provides rather important information by the change in fluorescence, which goes-together with the color change. For $Zn^{2+}$ ions the fluorescence of the surface gets changed from bright yellowish green to deep red. Intensity of fluorescence also provides significant information regarding the level of $Zn^{2+}$ ions in the sample. An intense red fluorescence indicates high level of $Zn^{2+}$ ions and low fluorescence indicates comparatively low level of $Zn^{2+}$ ions. All other biologically important metal ions like $Cu^{2+}$, $Fe^{2+}$, $Na^+$, and $K^+$ will result the fluorescence of the solid surface getting quenched or not changed. The device can be provided in the form of a kit.

The present assaying is simpler and, does not require sophisticated instruments. The device according to this invention comprises a thermoplastic or glass support strip which measures the presence of zinc ions in aqueous, clinical and analytical samples by measuring the fluorescence, wherein it is pre-coated with alumina in order to enable the adsorption of a zinc selective assay of the following formula (Formula 1).

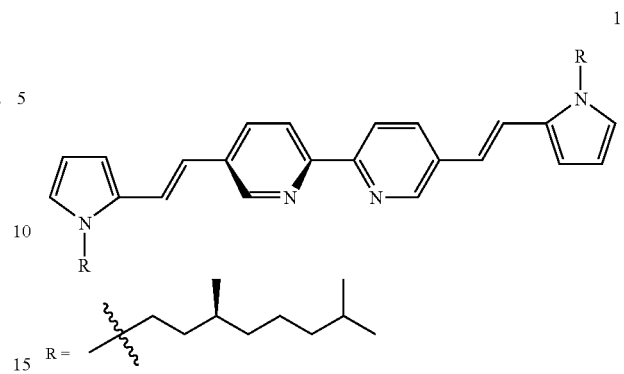

1

BRIEF DESCRIPTION ABOUT THE DRAWINGS

These and other features, aspects, and advantages of the present invention will become better understood with reference to the following description and appended claims and accompanying drawings where:

FIG. 1: Shows cartooned representation of the dipstick device. (1) Solid support (thermoplastic or glass) (2) Alumina coating containing assay (formula 1) (3) Zoomed portion of the surface clearly showing alumina which contains the assay (formula 1).

Figure 2:
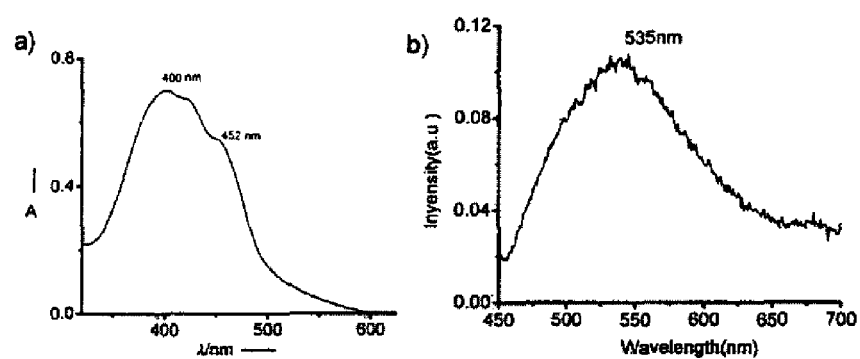

FIG. 2: a) Absorption and b) emission spectra of 1($6 \times 10^{-6}$ M) in acetonitrile.

FIG. 3: Solid state a) absorption and b) emission spectra of 1 (in PMMA matrix)

FIG. 4: Benesi-Hildebrand, Job Plot for $Zn^{2+}$ ions and selectivity plot, for assay 1 in acetonitrile.

Figure 5:
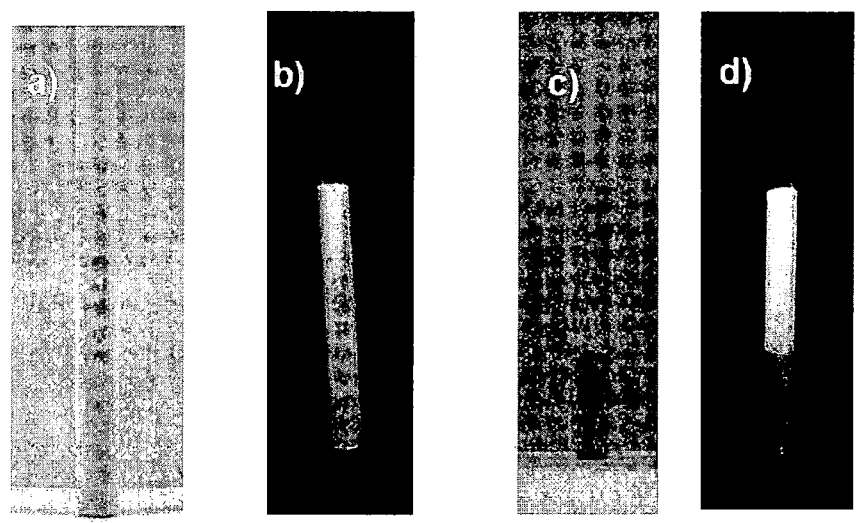

FIG. 5: Photograph of the performance of the device with $Zn^{2+}$ ions in aqueous medium a) photograph of the device in visible light, b) photograph of device illuminated by 365 nm UV light.

Figure 6:
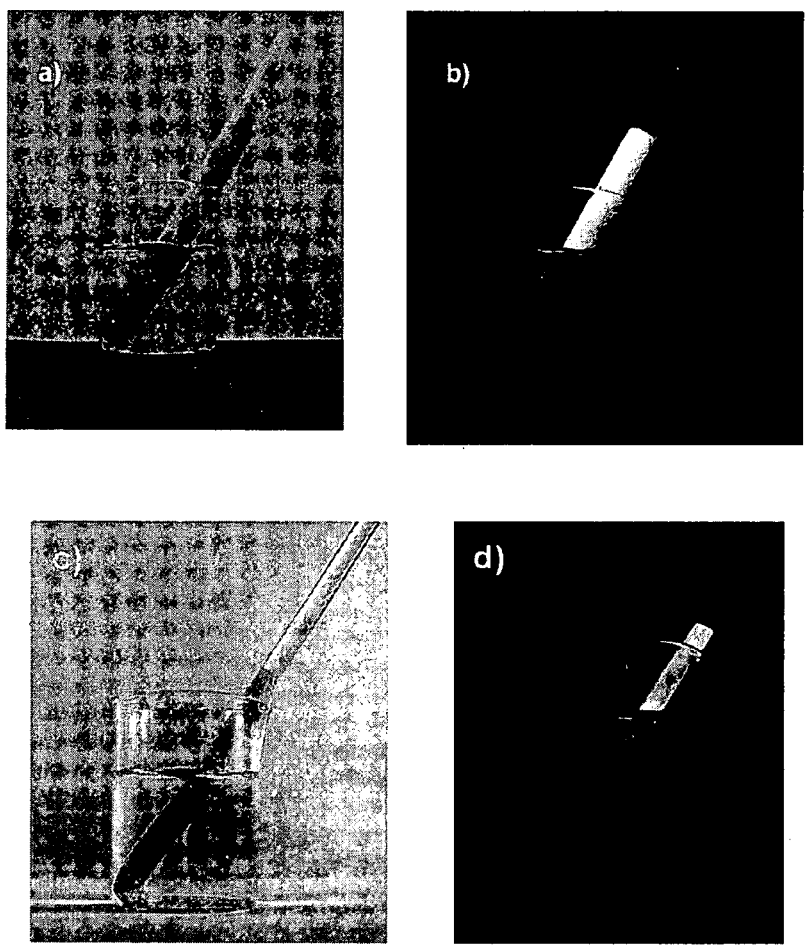

FIG. 6: Photograph of the dipstick device showing its performance in aqueous solution of zinc perchlorate [$5 \times 10^{-4}$ M]; a & b) dipstick prepared using thermoplastic support, c & d) device prepared using glass support; a & c) under visible light, b &d) illuminated under 365 nm UV light.

Figure 7:
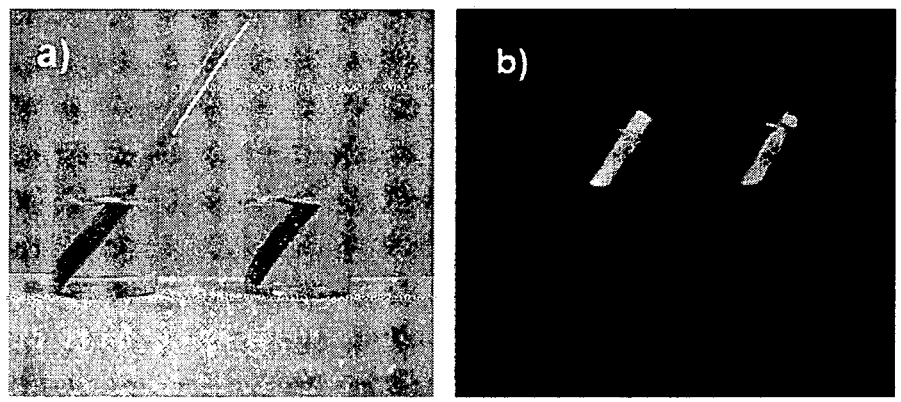

FIG. 7: Comparing performance of the present dipstick with zinc solution and $Cu^{2+}$ solution. a) under visible light, b) under 365 nm UV light illumination.

Figure 8:
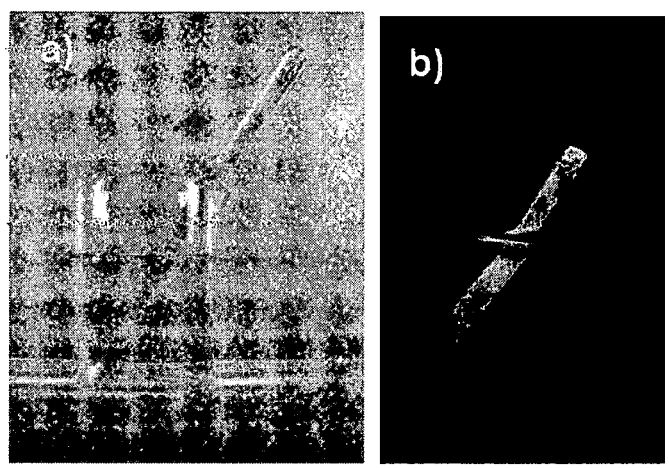

FIG. 8: Photograph showing the performance of the device with a solution containing metal ions like $Na^+$, $K^+$, $Ca^{2+}$, $Mg^{2+}$ etc. a) visible light b) 365 nm UV light.

Figure 9:
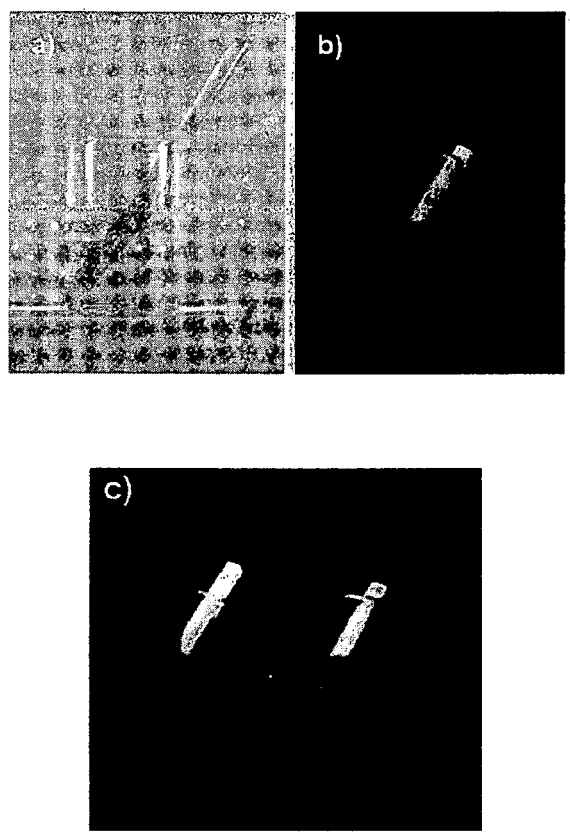

FIG. 9: Photograph of the device showing its performance in $Fe^{2+}$ solution. a) under visible light, b) under 365 nm UV illumination c) comparing the performance of dipstick with $Hg^{2+}$ and $Zn^{2+}$ under 365 nm UV light.

Figure 10:
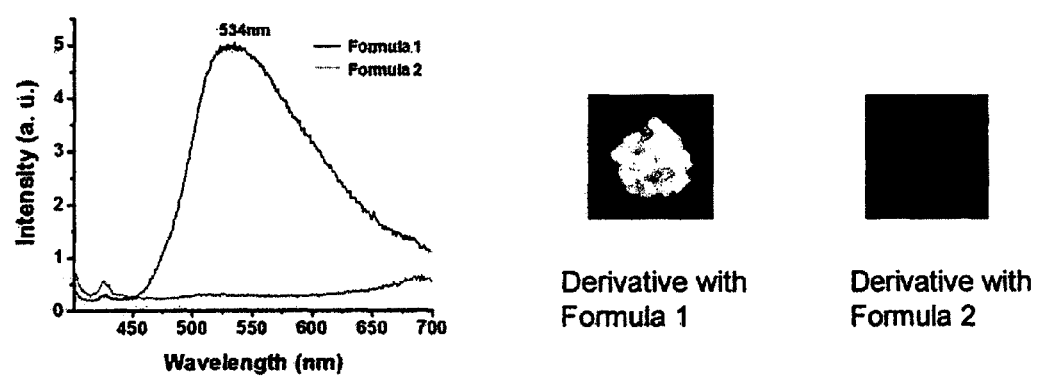

FIG. 10: Graph and photographs showing the difference in luminescence between the molecules of formula 1 and formula 2.

DETAILED DESCRIPTION OF THE INVENTION

To evaluate the amount of $Zn^{2+}$ ions in biological samples and analytical samples, the present invention comprises of:
1) pyrrole end-capped bipyridine assay having a general formula 1.
2) a practical device called "dipstick device" in which the assay is conveniently loaded.

3) binding of the metal ions into the assay (formula 1) attached over the surface of the dipstick and the binding event can be signaled by the change in color over the surface of the dipstick.
4) discrimination between $Zn^{2+}$ ions and other ions is by the visual change in the fluorescence in the surface of the stick with the help of a 365 nm UV-light. The change in the fluorescence is the result of metal ion binding to the assay adsorbed over the surface of the dipstick.
5) detecting said signal wherein said signal is proportional to the presence as well as the amount of $Zn^{2+}$ ions.
6) reusable nature of the said dipstick makes it more convenient and user friendly.

The solid surface can be any solid surface, which do not have any self-fluorescence which include thermoplastic, non-fluorescent membranes, absorption pads, glass rods and like. Preferred supports are thermoplastic and glass, which may be conveniently used by testing personnel, having minimal or no previous experience or training. The preparation and use of such test systems were well described in the patent and scientific literatures. Reference may be made to: (a) U.S. Pat. No. 6,406,862 B1, (b) Y. Takahashi, H. Kasai, H. Nakashini, T. M. Suzuki, *Angew. Chem. Int. Ed.,* 2006, 45, 913). If a stick is used, the assay (formula 1) adsorbed in alumina is bound to one end of the stick such that the end with the assay in alumina can be dipped into sample solution as described for the detection of all metal ions. The assay is carefully allowed to adsorb over alumina and it is coated over thermoplastic or glass support. Thereby prepared device is ready to use and can dip into analytical solutions containing metal ions. The concentration of metal ions can be as low as $5 \times 10^{-4}$ M and above.

The following MATERIALS and METHODS were used in the examples that follow: Thermoplastic or glass supports were cut into small units having 10 cm length and 4 mm radius. This can be prepared in variable length depending upon the nature of the samples to be analyzed. 10 mg of assay 1 (Formula 1) dissolved in 15 ml chloroform, to this solution add 2 gm of finely powdered alumina and allow 10 minutes for the solvent to evaporate off. The assay containing finely powdered alumina is yellow in color and having a greenish yellow fluorescence. The fine powdered alumina is bound over the stick up to 5 cm from the bottom of the stick (FIG. 1 and FIG. 5). Agitation of the dipstick in the test sample is preferred to enhance contact between the test area and the analyte to be detected. It has been found that the agitation decreases the time necessary for the assay presumably due to the overall increased analyte porous material contact. In addition if the test is conducted in a viscous fluid, more consistent results are achieved with agitation. Agitation can be done manually or mechanically and may be by motion of the dipstick or test sample or both. The present dipstick is reusable. The dipstick removed from the test sample is rinsed in aqueous EDTA solution, preferably by holding the bottom of the stick under EDTA solution in a small beaker. After EDTA treatment wash the stick with pure water and now it is ready for another application. Fluorescence as well as color changes over the surface of the stick can be visually graded or photograph can toe taken for permanent record.

In the present invention we have synthesized an analogous molecule which contains a chiral (asymmetric) carbon atom in the side chain. We found that this molecule of formula 1 has very high solid state luminescence (25 times higher) than the previously reported molecule of formula 2 which has very weak solid state luminescence. The high solid state luminescence of the new molecule makes them suitable for the design of a practical reusable dipstick for the detection of zinc ions under aqueous conditions. This difference in the luminescence property can seen in the following figure which shows solid state emission spectra of both derivatives formula 1 and formula 2 and the photograph of solid state luminescence of derivative having formula 1 with chiral side chain and derivatives having formula 2.

The following examples are given by way of illustration and therefore should not be construed to limit the scope of the present invention in any way.

EXAMPLE-1 a) Preparation of 5,5'-bis(bromomethyl)-2,2'-bipyridine (bisbromomethyl)

To a solution of 5,5'-dimethyl-2,2'-bipyridine (10 mmol) in 50 mL of dry carbontetrachloride was added N-bromosuccinimide (20.5 mmol) and AIBN (Azobisisobutyronitrile). The reaction Mixture was refluxed for 18-20 h., cooled, filtered and the solvents were removed under reduced pressure to give the crude product which was further purified by recrystallization from $CCl_4$. Yield 80-90%; mp. 188° C.; $^1$H NMR ($CDCl_3$, 300 MHz) δ 4.53 (s, 4H, $CH_2Br$), 7.79 (m, 2H, aromatic), 8.34 (m, 2H, aromatic), 8.61 (m, 2H, aromatic). $^{13}$C NMR ($CDCl_3$, 75 MHz) δ 29.43, 121.25, 133.28, 137.70, 149.27, 155.19.

b) Preparation of the 5,5'-Bis-(diethyl phosphonomethyl)-2,2'-bipyridine (Bisphosphonate)

Bisphosphonate were prepared by the reaction of the corresponding bisbromomethyl derivatives (2 mmol) with 3 mL of triethyl phosphite at 80-85° C. for 10-12 h followed by the removal of the unreacted triethyl phosphite by vacuum. Yield 90-95%; $^1$H NMR ($CDCl_3$, 300 MHz) δ 1.12 (m, 12H, $CH_3$), 3.21 (s, 4H, $CH_2P$), 4.14 (m, 8H, $OCH_2$), 7.34 (m, 2H, aromatic), 8.01 (m, 2H, aromatic), 8.30 (m, 2H, aromatic).

EXAMPLE-2

Preparation of the Assay Having Formula 1

A suspension of sodium hydride (12 mmol) in dry THF was added slowly to a solution of the bisphosphonate (2 mmol) (Example 1b) and the respective N-alkylpyrrole-2-carboxaldehyde (4 mmol) in THF. After refluxing for 12 h the highly fluorescent reaction mixture obtained was cooled followed by the removal of the THF under reduced pressure to give a pasty residue. The residue was suspended in water and extracted with dichloromethane. The organic layer was washed with brine, dried over $Na_2SO_4$ and concentrated to give the crude product, which was further purified by column chromatography over silica gel using petroleum ether as eluent. Yield 40-45%; mp. 82° C.; IR (KBr) $v_{max}$ 2925, 2853, 1699, 1626, 1467, 1209, 1045, 950, 850, 727 $cm^{-1}$; $^1$H NMR ($CDCl_3$, 300 MHz) δ 0.89 (m, 12H, $CH_3$), 1.28 (m, 16H, $CH_2$) 1.76 (m, 2H, CH), 3.93 (m, 4H, $NCH_2$), 6.17 (t, 2H; aromatic), 6.58 (d, 2H, aromatic), 6.67 (s, 2H, aromatic), 6.87 (d, 2H, vinylic, J=16.07 Hz), 7.07 (d, 2H, vinylic, J=16.08 Hz), 7.85 (m, 2H, aromatic), 8.34 (d, 2H, aromatic), 8.70 (s, 2H, aromatic); $^{13}$C NMR ($CDCl_3$, 75 MHz) δ 10.63, 13.98, 22.94, 23.86, 28.56, 29.65, 30.54, 41.27, 50.88, 107.34, 108.37, 119.16, 120.70, 121.20, 1124.08, 130.96, 132.58, 133.53, 147.36, 153.87.

EXAMPLE-3

Thermoplastic or glass support was cut as shown in FIG. 5, as 10 cm long and having 4 mm radius. Assay containing alumina is carefully fixed over the surface of the support and the said dipstick is ready to use. A 25 ml beaker containing zinc perchlorate solution ($5\times10^{-4}$ M) is taken and the stick is dipped in it, followed by the agitation of the stick in the solution. Wherever the analyte is in contact with the stick a color change will be observed from yellow to orange red, which indicates the presence of metal ions. If the color change is followed by intense change in the fluorescence from greenish yellow to deep red it indicates in specific the presence of zinc ions (FIGS. 5 and 6). The dipstick removed from the test sample is rinsed in aqueous EDTA solution, preferably by holding the bottom of the stick under EDTA solution in a small beaker. After EDTA treatment wash the stick with pure water and now the stick is ready for another application.

EXAMPLE-4

The assay based on pyrrole end-capped bipyridine (formula 1) can be used quantitatively in solution state for selective detection of $Zn^{2+}$ in acetonitrile. The assay formula 1 showed strong emission around 537 nm in acetonitrile with a quantum yield of 0.4. Titration of transition metal salts to assay with formula 1 showed strong quenching of the emission at 537 nm except in the case of $Zn^{2+}$, which resulted in a red-shifted emission at 637 nm. Alkali and alkaline earth metal salts could not induce any considerable changes to the emission behavior of assay. The binding of $Zn^{2+}$ was highly selective in the presence of a variety of other metal ions. Though $Cu^{2+}$ quenches the emission of 1, in the presence of $Zn^{2+}$, a red emission prevails, indicating the preference of 1 toward $Zn^{2+}$. Job plot and Benesi-Hildebrand analysis revealed a 1:1 complexation between the probe and the metal ion (Benesi-Hidebrand, Job plot and selectivity plot in FIG. 4).

The main advantages of the present invention are:
1) The excellent selectivity shown by the assay with formula 1 towards $Zn^{2+}$ ions among other biologically important metal ions like $Na^+$, $K^+$, $Mg^{2+}$, $Ca^{2+}$, $Cu^{2+}$, $Fe^{2+}$, $Hg^{2+}$ etc. The binding event can be distinguished by color change along with intense changes in the fluorescence of assay, which is affixed in the alumina matrix. This provides rather valuable and distinguishable information about to easily discriminate zinc ions from other metal ions. The fluorophore affixed in the alumina matrix is having high quantum yield value in solid state ($\phi_f$=0.46) (FIGS. 3 & 5) and is water insoluble. The zinc selective assay 1 adsorbed over alumina containing hydrophobic chiral side chains, which offers the required hydrophobicity to prevent leaching of the probe in aqueous samples. Albeit the fluorophore is water insoluble, it interacts with metal ions in the aqueous medium of the sample.
2) The pyrrole end capped bipyridine assay in acetonitrile solution can be used to quantify the amount of zinc ions in solutions, using spectroscopic techniques like UV-spectrophotometer and fluorimeter. In addition to this, the assay having formula 1 can be more conveniently used as a device by coating the assay in alumina over a thermoplastic or a glass solid support.
3) The present invention make the fabrication of present device is so comfortable that it can handle and use very easily and needs no expertise or sophisticated machineries.
4) The reversibility of the present assay (ie; the reusability) is another promising aspect of this invention for its practical application. The probe which is once used can be used again by washing the probe in EDTA (ethylene diamine tetra acetic-acid) solution, since EDTA is a strong chelator to metal ions like $Zn^{2+}$ and $Cu^{2+}$. The dipstick design in the present invention can also be used as rapid detection strips in viscous fluids or in the fluids containing cellular or particulate materials, where the contact between the test sample and the assay support may be impaired or reduced.

What is claimed is:
1. Pyrrole end capped bipyridine of Formula 1

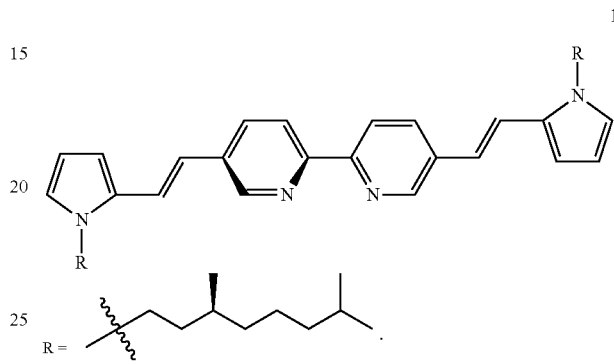

2. A product comprising the pyrrole end capped bipyridine according to claim 1.
3. A process for the preparation of pyrrole end capped bipyridine of formula 1

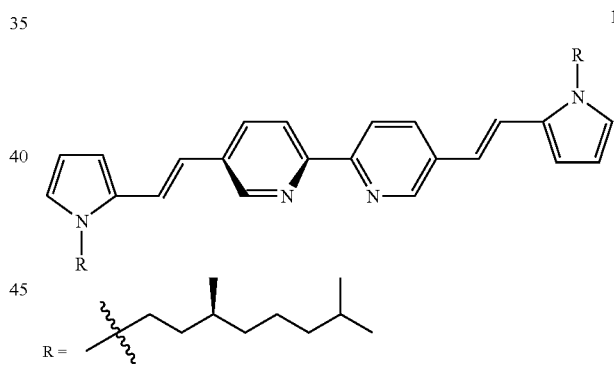

and said process comprising the steps of:
a) preparing 5,5'-bis(bromomethyl)-2,2'-bipyridine by reacting 5,5'-dimethyl-2,2-bipyridine in dry carbon tetrachloride in the presence of N-bromosuccinimide,
b) preparing 5,5'-Bis-(diethyl phosphonomethyl)-2,2'-bipyridine by reacting 5,5'-bis(bromomethyl)-2,2'-bipyridine obtained in step (a) with triethyl phosphite,
c) reacting 5,5'-Bis-(diethyl phosphonomethyl)-2,2'-bipyridine obtained obtained in step (b) with N-alkylpyrrole-2-carboxaaldehyde of formula 1'

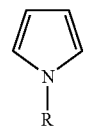

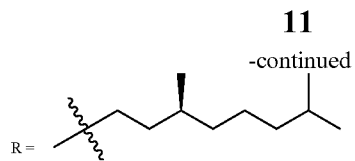

in a molar ratio of 1:2 to 1:3, in the presence of sodium hydride in dry tetrahydrofuran (THF), under reflux, for a period of 10 to 20 hours, d) cooling the reaction mixture of step (c) to a temperature of 25° C. to 35° C. and removing the THF solvent under reduced pressure to obtained a pasty residue, e) suspending the pasty residue in water and extracting it with dichloromethyl, followed by washing the organic layer with brine, and f) drying and concentrating the washed organic layer to obtain the pyrrole end capped bipyridine of formula 1.

4. A process according to claim 3, wherein the molar ratio of bisphosphonate to N-alkylpyrrole-2-carboxaaldehyde used in step (c) is 1:2.

5. A process according to claim 3, wherein the reaction time period used in step (c) is in the range of 12 to 14 hours.

6. A process according to claim 3, wherein the overall yield of the pyrrole end capped bipyridine of formula 1 obtained is in the range of 40% to 45%.

7. A process according to claim 3, wherein the pyrrole end capped bipyridine of Formula 1 exhibits a highly greenish yellow solid state illuminations.

8. A process according to claim 3, wherein the pyrrole end capped bipyridine of Formula 1 exhibits strong emission in acetonitrile at about 537 nm at a quantum yield of 0.4.

9. A dipstick device useful for the selective detection of $Zn^{2+}$ ions in solution comprising:

a strip support having deposited thereon pyrrole end capped bipyridine of Formula 1 adsorbed over the ceramic powder preferably alumina

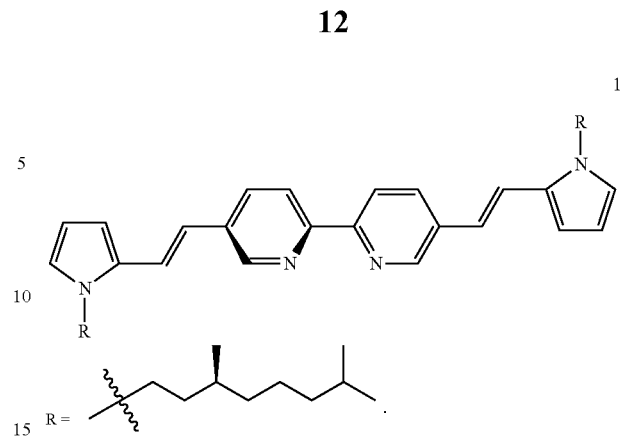

10. A dipstick device according to claim 9 wherein the strip support used is made of plastic, glass or paper backing.

11. A dipstick device according to claim 9 which is useful for the detection of $Zn^{2+}$ ions in solution.

12. A dipstick device according to claim 9 is useful for the quantitative detection of the lowest Zn metal ions concentration of $5 \times 10^{-4}$ M.

13. The pyrrole end capped bipyridine of claim 1 in powder form.

14. The product of claim 2, wherein the pyrrole end capped bipyridine is a powder.

15. A process according to claim 3, further comprising the step of purifying the pyrrole end capped bipyridine of formula 1.

* * * * *